United States Patent [19]

Chatburn et al.

[11] Patent Number: 4,589,409

[45] Date of Patent: May 20, 1986

[54] HEAT AND HUMIDIFICATION SYSTEM FOR HIGH FREQUENCY JET VENTILATION

[76] Inventors: Robert L. Chatburn, 3135 E. Derbyshire, Cleveland Heights, Ohio 44118; Marvin D. Lough, 307 Eastoverlook Dr., Eastlake, Ohio 44094

[21] Appl. No.: 546,652

[22] Filed: Oct. 28, 1983

[51] Int. Cl.$^4$ ............................................. A61M 16/00
[52] U.S. Cl. ............................ 128/203.26; 128/204.25
[58] Field of Search ..................... 128/203.12, 203.16, 128/203.17, 203.26, 203.27, 204.13, 204.14, 204.17, 200.21, 200.18

[56] References Cited

U.S. PATENT DOCUMENTS

| | | |
|---|---|---|
| 3,071,131 | 1/1963 | Johannisson et al. |
| 3,434,471 | 3/1969 | Liston |
| 3,669,108 | 6/1972 | Sundblom et al. |
| 3,714,944 | 2/1973 | Price et al. |
| 3,789,837 | 2/1974 | Philips et al. |
| 3,820,539 | 7/1974 | Ollivier |
| 3,912,795 | 10/1975 | Jackson |
| 3,985,131 | 10/1976 | Buck et al. |
| 4,038,980 | 8/1977 | Fodor .......................... 128/203.27 |
| 4,051,205 | 9/1977 | Grant ........................... 128/204.14 |
| 4,116,228 | 9/1978 | Hudspeth et al. |
| 4,121,581 | 10/1978 | Schmader |
| 4,163,450 | 8/1979 | Kirk et al. |
| 4,201,204 | 5/1980 | Rinne et al. .................. 128/203.27 |
| 4,206,754 | 6/1980 | Cox et al. |
| 4,249,527 | 2/1981 | Ko et al. |
| 4,305,388 | 12/1981 | Brisson |
| 4,333,451 | 6/1982 | Paluch |
| 4,336,798 | 6/1982 | Beran |

OTHER PUBLICATIONS

S. Derderian et al., High Frequency Positive Pressure Jet Ventilation in Bilateral Brochopleural Fistulae, *Critical Care Medicine*, vol. 10, No. 2, Feb. 1982, 119–121.
M. Klain et al., High Frequency Ventilation, papers presented at the High Frequency Ventilation Symposium on Apr. 10, 1981.
G. Carlon et al., Clinical Experience with High Frequency Jet Ventilation, *Critical Care Medicine*, vol. 9, No. 1, Jan. 1981, 1–6.
A. Slutsky et al., Effective Pulmonary Ventilation with Small–Volume Oscillations at High Frequency, *Science*, vol. 209, 1, Aug. 1980, 609–611.
H. Keszler et al., Tracheobronchial Toilet Without Cardiorespiratory Impairment, *Critical Care Medicine*, vol. 8, No. 5, May 1980, 298–301.
G. Carlon et al., Technical Aspects and Clinical Implications of High Frequency Jet Ventilation with a Solenoid Valve, *Critical Care Medicine*, vol. 9, No. 1, Jan. 1981, 47–50.
P. Scherer et al., Bronchial Bifurcations and Respiratory Mass Transport, *Science*, vol. 208, 4, Apr. 1980, 69–71.
M. Klain et al., High Frequency Percutaneous Transtracheal Jet Ventilation, *Critical Care Medicine*, vol. 5, No. 6, Nov. Dec. 1977, 280–287.
R. L. Chatburn et al., A Heat and Humidification System for High Frequency Jet Ventilation, vol. 27, No. 11, Nov. 1982.
U. H. Sjostrand et al., Volume–Controlled High–Frequency Positive–Pressure Ventilation as a Useful Mode of Ventilation During Open-Chest Surgery—A Report of Three Cases, vol. 27, No. 11, Nov. 1982.
R. B. Smith, Editorial, Humidification During High Frequency Ventilation, vol. 27, No. 11, Nov. 1982.
Jet Ventilator Advertisement in *Health Industry Today*, Feb. 1983.

*Primary Examiner*—Henry J. Recla
*Attorney, Agent, or Firm*—Emch, Schaffer, Schaub & Porcello Co.

[57] ABSTRACT

The present invention is directed to a high frequency jet ventilator humidification system which generally includes an air-oxygen blender, a heat exchanger, a solenoid valve, a water infusion pump, a humidifier, and a small tube coaxially positioned in a larger tube for delivery of respirable gas to a patient.

3 Claims, 6 Drawing Figures

HEAT AND HUMIDIFICATION SYSTEM FOR HIGH FREQUENCY JET VENTILATION

BACKGROUND OF THE INVENTION

The present invention relates to a heat and humidification system for use with a high frequency jet ventilator humidification system in delivering respirable gas to the lungs of a patient. While the use of high frequency jet ventilator in a variety of clinical situations is gaining increased acceptance in the medical profession, there are still important technical problems to be solved in the heating and humidification of the delivered gas. It has been found that conventional humidifiers are unsuitable in this application for at least two reasons: first, they are not designed to withstand the relatively high system pressures; and second, the compressible gas volumes of even the smallest infant humidifiers attenuate or damp the jet pulsations, thereby hampering their transmission to the patient's airways.

To avoid the problems of the convention humidifier, humidification of the delivered gas is sometimes accomplished by injecting water in droplet form into the gas from the jet ventilator with an infusion pump. In this technique, the water from the infusion pump can be heated but there is no provision for heating the jet gas. In such systems the jet ventilator is used with a separate circuit that provides heated and humidified gas at the point of connection to the patient's endotracheal tube. This allows the patient to breath conditioned gas during spontaneous respirations and permits independent control of continuous positive airway pressure. Some of the gas in the continuous positive airway pressure circuit may be entrained during the jet pulsations, thereby increasing the humidity and temperature of the gas delivered to the patient. In general, however, the gas reaching the patient's airways is cooler than body temperature, and most of the water it carries is delivered in particulate form. While these conditions may be acceptable for the high frequency jet ventilation of adults, they can cause problems of fluid overload, electrolyte imbalance, and hypothermia in premature infants and children. In addition, cold nebulized water and low inspired air temperatures may contribute to pulmonary damage during intermittent positive-pressure ventilation. Therefore, there is a need for an improved system which would condition the gas delivered by the jet ventilator so that the gas is free of particulate water but saturated with water vapor at body temperature.

In addition, it has been found that conventional humidifiers require a great deal of maintenance and repair. Often, the heat exchanger and delivery circuit are not reusable since they cannot be easily cleaned and sterilized. Thus, there is a need for an improved system which does not require a great deal of maintenance and repair. There is a further need for a system which is reusable and which can be easily cleaned and sterilized.

SUMMARY OF THE INVENTION

The present invention is directed to a high frequency jet ventilator humidification system which generally includes an air-oxygen blender, a heat exchanger, a solenoid valve, a water infusion pump, a humidifier and a small tube coaxially positioned in a larger tube for delivery of respirable gas to a patient.

The respirable gas used by the system of the present invention is supplied by an air-oxygen blender. The gas is delivered to a variable pressure regulator which pressurizes the gas. The pressurized gas, hereinafter referred to as jet gas, flows fom the variable regulator to a heat exchanger, which preheats the jet gas and delivers the pressurized, preheated jet gas to a solenoid valve. Water is added to the jet gas immediately after the gas leaves the solenoid valve by an infusion pump which is equipped with a one-way valve. This mixture of jet gas and infused water droplets is then returned to the heat exchanger where the water droplets are vaporized. The jet gas containing the vaporized water droplets is then delivered from the heat exchanger through a small bore tubing which is situated inside the continuous positive airway pressure circuit.

Gas also flows from the air-oxygen blender through a flowmeter which monitors the flow rate of the gas and delivers the gas to a conventional humidifier heater. The heated and humidified gas flows from the humidifier through the large bore tubing of the continuous positive airway pressure circuit. In the preferred embodiment the larger tubing has an interior diameter greater than the exterior diameter of the tubing used to transfer the jet gas. The jet gas tubing is contained within the larger diameter tubing, thereby enabling such heated and humidified continuous positive airway pressure gas to help maintain the temperature of the jet gas after the jet gas leaves the heat exchanger the second time.

Finally, the jet gas is delivered through a thermal connector, for example, a short length of brass tubing which is located near the patient connection point. The thermal connector includes a digital thermometer so that the temperature of the jet gas can be monitored as it passes through the thermal connector. The thermistor-tube junction is wrapped with insulation to prevent interference from ambient temperature fluctuations and the length of tubing that conducts jet gas through the thermistor connection is minimized to avoid cooling of the jet gas. The pressurized, preheated, humidified gas is then delivered to the patient through the endotracheal tube connector.

The primary object of the present invention is to provide an improved high frequency jet ventilator system which conditions the respirable gas delivered by the jet ventilator system such that the gas is free of particulate water, but which is saturated with water vapor at body temperature.

DESCRIPTION OF THE PREFERRED EMBODIMENT

The invention is directed to a high frequency jet ventilator for use in delivering respirable gas to the lungs of a patient. More particularly, the high frequency jet ventilator system includes a heat and a humidification system. The features of the invention will be more fully understood by referring to the attached drawings in connection with the following description of the invention.

Figure 1:
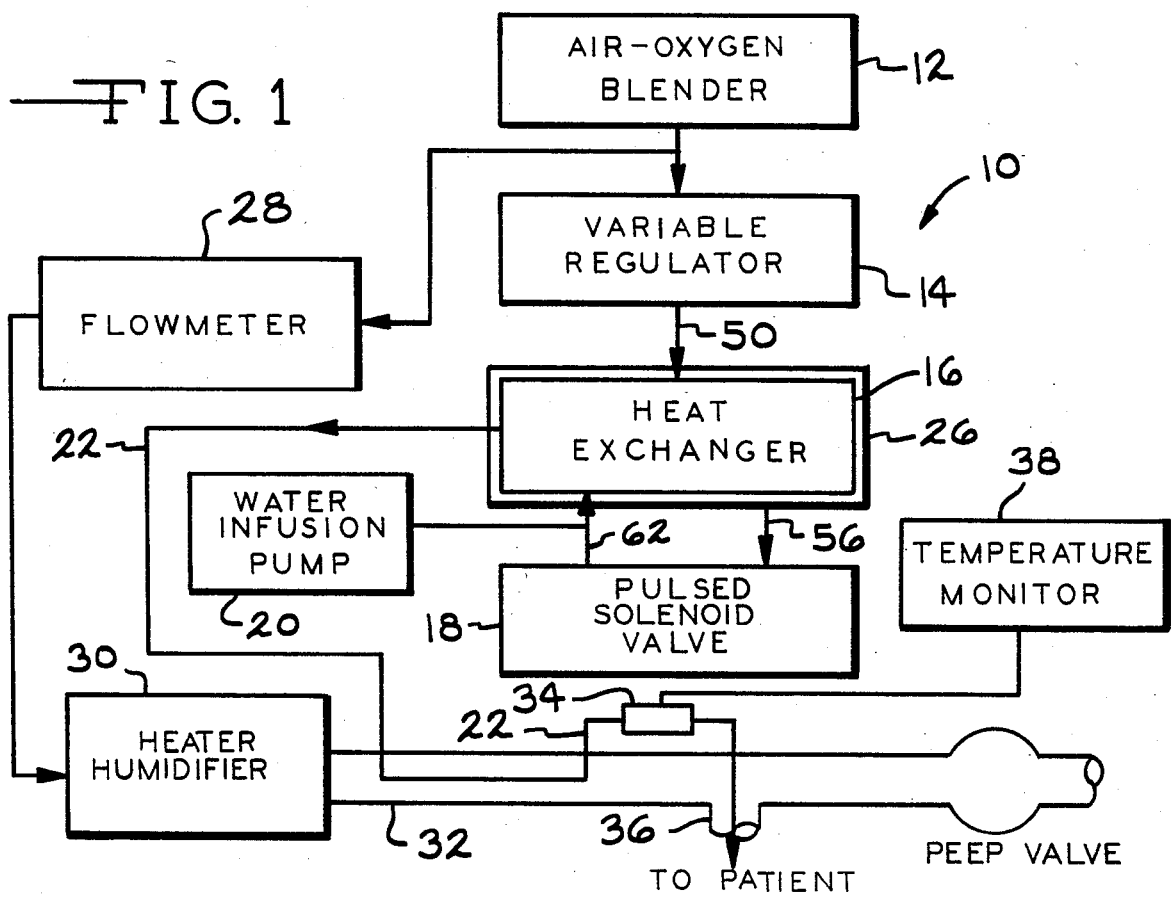
FIG. 1 is a block diagram of a ventilator humidification system showing the flow of gas through the ventilator system.
Figure 2:
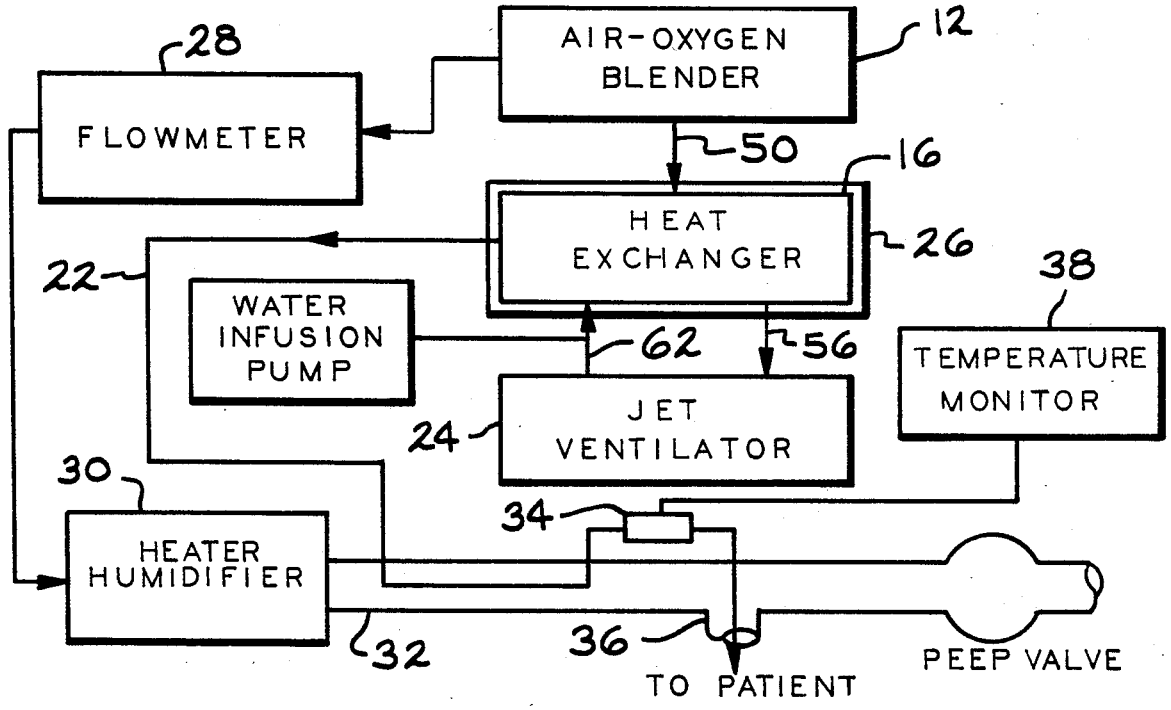
FIG. 2 is a block diagram, similar to FIG. 1, showing an alternative path of flow of the gas through the ventilator humidification system.

FIG. 1 is a block diagram of one embodiment of a high frequency jet ventilator humidification system 10 of the present invention. FIG. 2, is a block diagram of a second embodiment of a high frequency jet ventilator humidification system. The high frequency jet ventilator is generally comprised of a variable regulator, a solenoid valve, and a timer (not shown), and in the preferred embodiments, the variable regulator, the solenoid valve and timer are an integral unit. FIGS. 1 and 2 show different embodiments of connecting the high frequency jet ventilator with a heat exchanger.

Referring now to FIG. 1, the respirable gas used by the high frequency jet ventilator system 10 is supplied by an air-oxygen blender 12. The gas is delivered to a variable pressure regulator 14 which pressurizes the gas. This pressurized gas, hereinafter referred to as jet gas, flows from the variable regulator 14 to a heat exchanger 16. The jet gas is preheated in the heat exchanger 16 and is delivered to a solenoid valve 18. Water is added to the pressurized and preheated jet gas after the jet gas leaves the solenoid valve 18, by an infusion pump 20 which is equipped with a one-way valve (not shown). The mixture of jet gas and infused water droplets then passes back into the heat exchanger 16 where the infused water is vaporized. The jet gas is then delivered from the heat exchanger 16 through small-bore tubing 22 which is situated inside the continuous positive airway pressure circuit.

Gas also flows from the air-oxygen blender 12 through a flowmeter 28, which monitors the flow rate of the gas, to a conventional humidifier heater 30. The heated and humidified gas is delivered from the humidifier 30 through tubing 32 of the continuous positive airway pressure circuit. In the preferred embodiment the tubing 32 has an interior diameter greater than the outside diameter of a delivery tube 22 and delivery tube 22 is contained within tubing 32 such that the heated and humidified gas of the continuous positive airway pressure circuit helps to maintain the temperature of the jet gas.

The jet gas is then delivered to a short thermal connector 34 located near the patient connector point 36 so that the temperature of the jet gas can be monitored by a digital thermometer 38 having thermistor probe (not shown) attached to the thermal connector 34. A hole (not shown) drilled through the thermal connector 34 puts the thermistor in communication with the jet gas. The thermistor-tube junction is wrapped with insulation (not shown) to prevent interference with the temperature of the jet gas from ambient temperature fluctuations. Also the length of thermal connector 34 that conducts the jet gas through the thermistor connection, and that is exposed to room air is minimized to avoid cooling of the jet gas.

Figure 3:
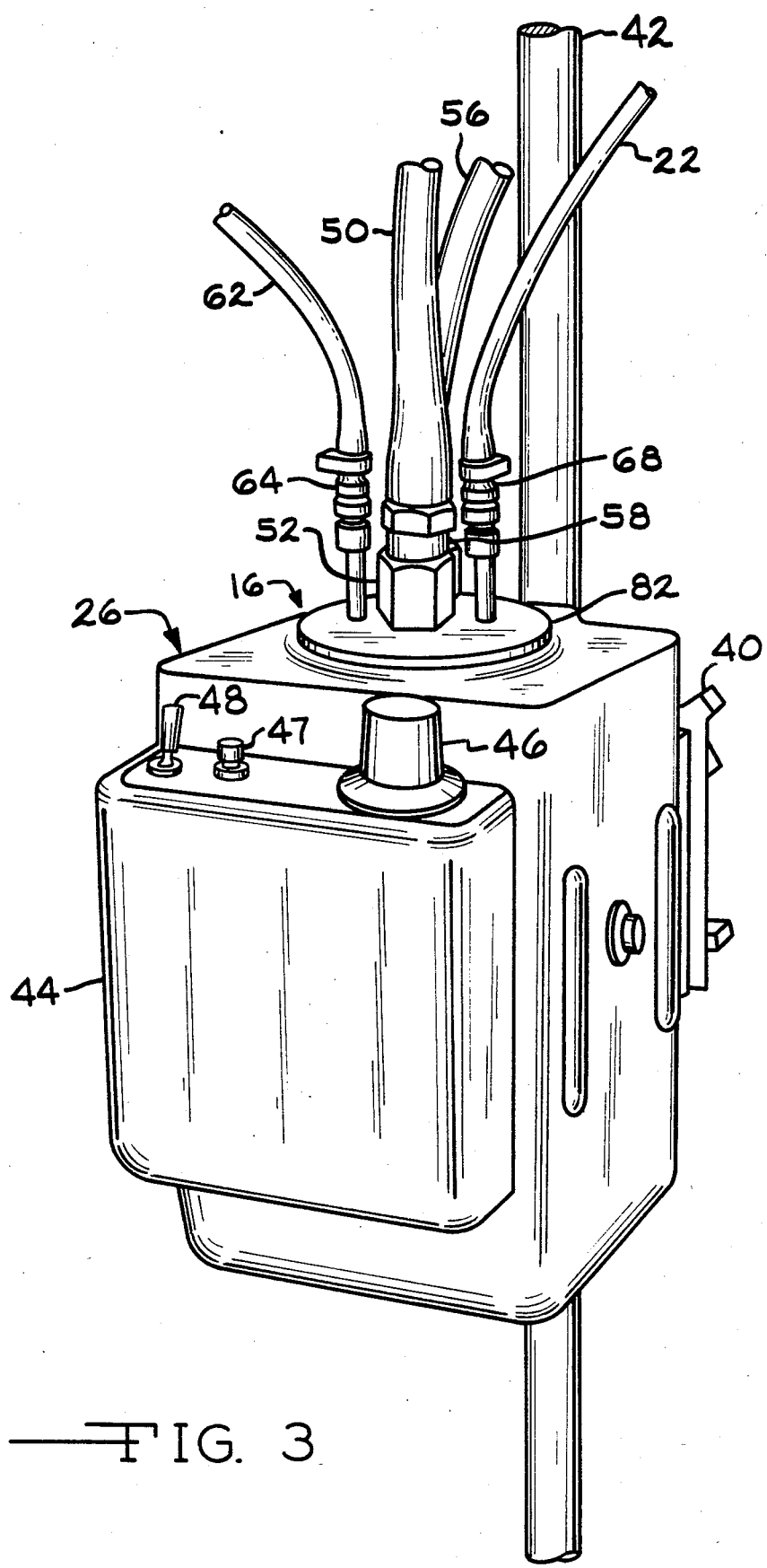
FIG. 3 is a perspective view showing a humidifier heater.

FIG. 3 shows the heat exchanger 16 positioned in the heat exchanger heater 26. The heat exchanger heater 26 is attached to a bracket 40 which is mounted on a bar 42 on the high frequency jet ventilation humidification system 10. The heat exchanger heater 26 includes a control box 44, which includes a thermostat 46, an indicator light 47 and an on/off switch 48, and is used to control the fluctuations in the heat and humidity of the high frequency jet ventilation humidification system 10. The jet gas flows from the variable regulator 14 through a high pressure hose 50 into a first chamber 60 of the heat exchanger 16. The hose 50 is connected to the heat exchanger 16 with a lock nut mechanism 52. The jet gas flows through the chamber 60 and exits through a second high pressure hose 56. The first end of high pressure hose 56 is connected to the heat exchanger 16 with a lock nut mechanism 58. The hose 56 operatively connects the heat exchanger 16 with the solenoid valve 18. As the jet gas leaves the solenoid valve 18 water is added to the jet gas by the water infusion pump 20. The jet gas/water mixture flows through a tube 62 connected to the heat exchanger 16 by fitting 64 and enters a second chamber 70 within the heat exchanger 16. The water in the jet gas/water mixture vaporizes in the second chamber 70 of the heat exchanger 16 and the mixture leaves the second chamber 70 via the delivery tube 22, which is also connected to the heat exchanger 16 by fitting 68. The delivery tube 22 has a relatively small inside diameter of typically no more than ⅛ inch. The delivery tube 22 is positioned inside the tubing 32 of the continuous positive airway pressure circuit. The heated and humidified gas which flows through the tubing 32 from the humidifier heater 30 acts to help maintain the temperature of the jet gas/vaporized water mixture in the delivery tube 22.

Jet gas is conducted through the preheating chamber 60 of the heat exchanger via high pressure hoses 50 and 56. These hoses 50 and 56 can be connected to the jet ventilator in one of two preferred manners. For instance, referring now to FIG. 1 hose 50 connects the output of the variable regulator to the heat exchanger 16 and hose 56 connects the heat exchanger 16 to the solenoid valve 18. Alternatively, referring now to FIG. 2 hose 50 connects the output of the air-oxygen blender 12 to the heat exchanger 16 and hose 56 connects the heat exchanger 16 to the high pressure inlet of the jet ventilator 24. In the embodiments shown separate heaters (heat exchanger 26 and humidifier 30 respectively) are used to heat the jet gas and the continuous positive airway pressure circuit gas. it should be understood, however, that one heater can be designed for the dual purpose of use with the heat exchanger 16 to heat the jet gas and with the humidifier 30 to heat the gas of the continuous positive airway pressure circuit.

Figure 4:
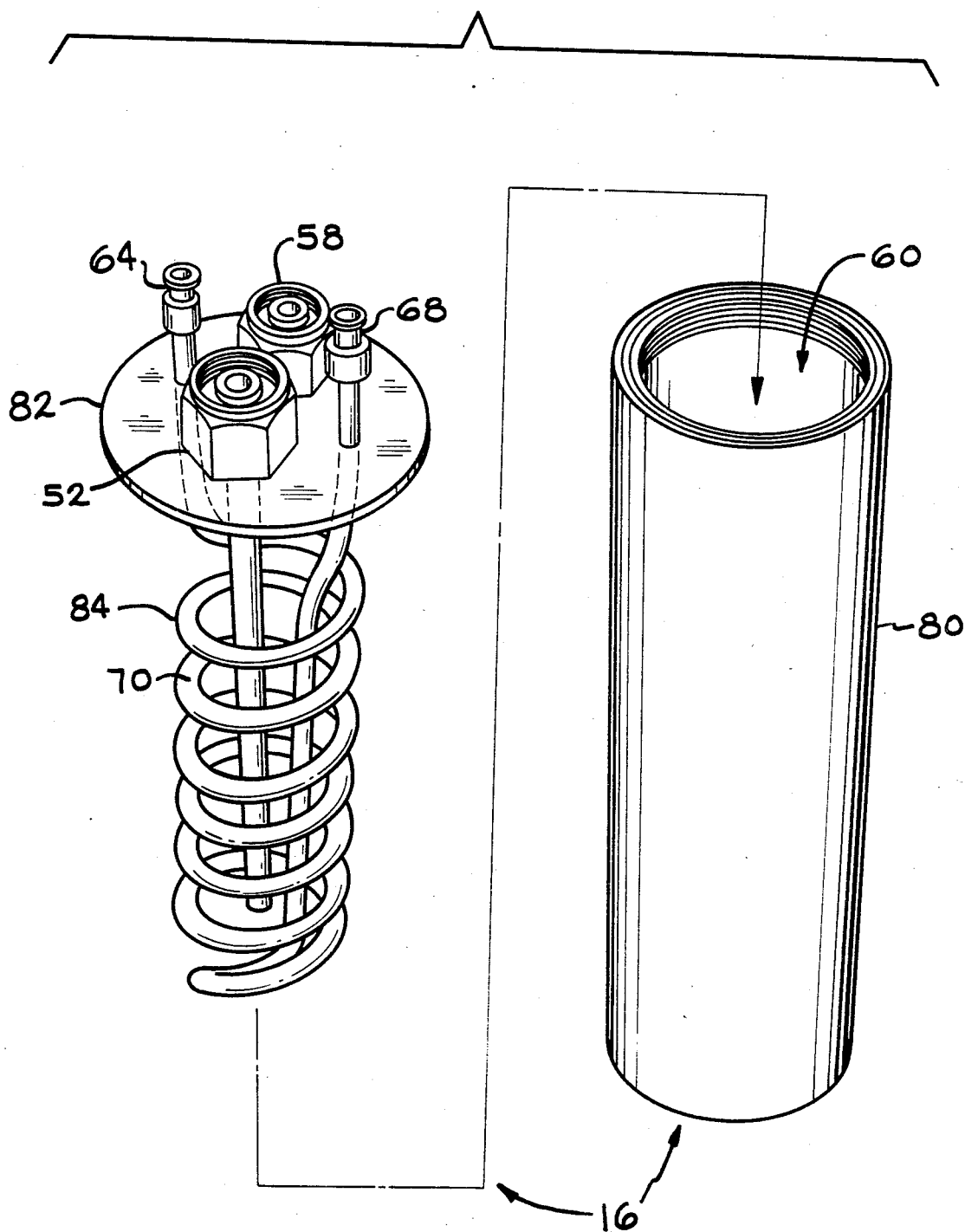
FIG. 4 is an exploded perspective view showing a heat exchanger.

Referring now to FIG. 4 the heat exchanger 16 will be described. The heat exchanger 16 includes a canister 80 with a tight-fitting, removable lid 82. Fastened to the lid 82 and suspended in the canister 80 is tubing 84 formed into a coil which defines second chamber 70. The heat exchanger unit 16 is inserted into the heater 26 and receives heat therefrom. Jet gas coming from the solenoid valve 18 in hose 62 receives water from the infusion pump 20 and enters the heat exchanger 16 through fitting 64. The jet gas containing the infused water travels through the second chamber 70 defined by coiled tubing 84. Heat received from the heater 26 vaporizes the infused water as the jet gas travels through coiled tubing 84. The resulting heated and humidified jet gas then exits the coiled tubing 84 through the delivery tube 22 and passes through the continuous positive airway pressure circuit as previously described herein.

Figure 5:
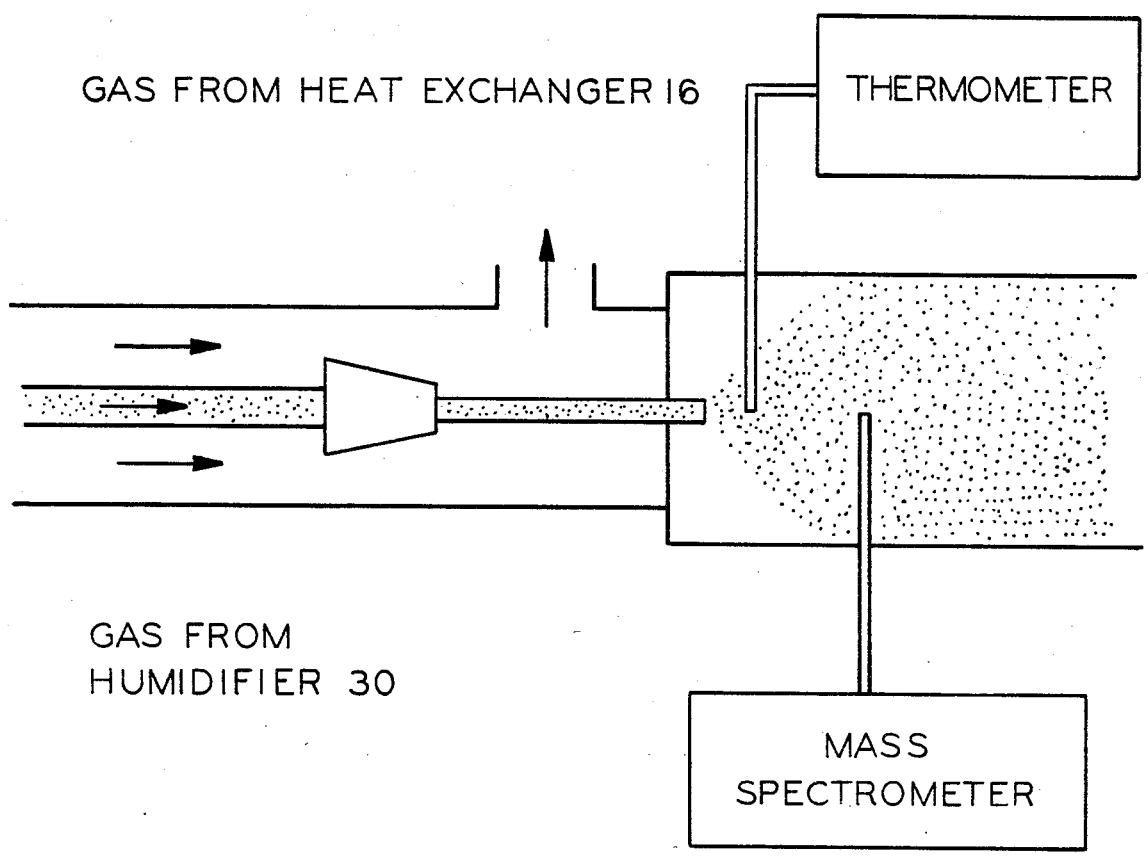
FIG. 5 is a block diagram, showing the apparatus used to measure the temperature and humidity of the jet gas.

The operation of the system of the present invention, specifically the temperature and humidity of the jet gas have been experimentally measured using the apparatus shown in FIG. 5. The delivery tube 22 is connected to a 2 ½", 14-gauge angiocath 90. The larger-bore tubing 32, in which the delivery tube 22 wa placed, was connected to the humidifier 30. The jet gas delivered through the catheter 90 was directed into a small insulated sample chamber 92 containing a temperature probe 94 and a mass spectrometer probe 96. The mass spectrometer system for water vapor measurement was specially designed to provide a 10–90% response time of 250 ms to step changes in water vapor. This measurement, in conjunction with the temperature measurement, provided data for the calculation of relative humidity (RH), which was calculated as the ratio of the measured water vapor pressure to the vapor pressure of saturated gas at the measured temperature. The absolute humidity was estimated by multiplying the calculated RH by the water vapor content of saturated gas at the measured temperature. The temperature of the jet gas before it reached the angiocath was monitored as described above. For all experiments the jet ventilator was set at a frequency of 150/min with a duty cycle of 30% and a total jet flow of 8 l/min. The duty cycle is the ratio of the time that the solenoid valve is on, allowing gas to flow through it, to the time spent for one complete on-off cycle and is expressed as a percent. The total jet flow is the amount of gas delivered through the 14-gauge catheter per minute. The driving pressure, set by the variable pressure regulator, was 18 psi.

In the first series of measurements no attempt was made to heat the jet gas with either the heat exchanger or the continuous positive airway pressure circuit so that the technique of humidification by injection of water into a delivery tube could be assessed without heating of the jet gas. In the next series of measurements the temperature and RH of the jet gas were optimized. The temperature of the continuous positive airway pressure gas, measured at the point of connection to the sampling chamber, was maintained at or near 37° C. Water was injected at flowrates from 5–25 ml/h, and the humidifier heater 30 was adjusted to raise the temperature of the jet gas as close as possible to 37° C. The resulting water vapor pressures of the jet gas were recorded.

With the unheated system, particulate water was visible at all times on the walls of the jet delivery tubing regardless of the injected water flowrates used. This resulted in a high RH (93% at 5 ml/h), but the temperature of the inspired gas dropped as low as 17° C.

When the system was heated, particulate water was not visible on the walls of the delivery tube at injected water flowrates below 22 ml/h but became visible as injection rates were increased above that value.

Figure 6:
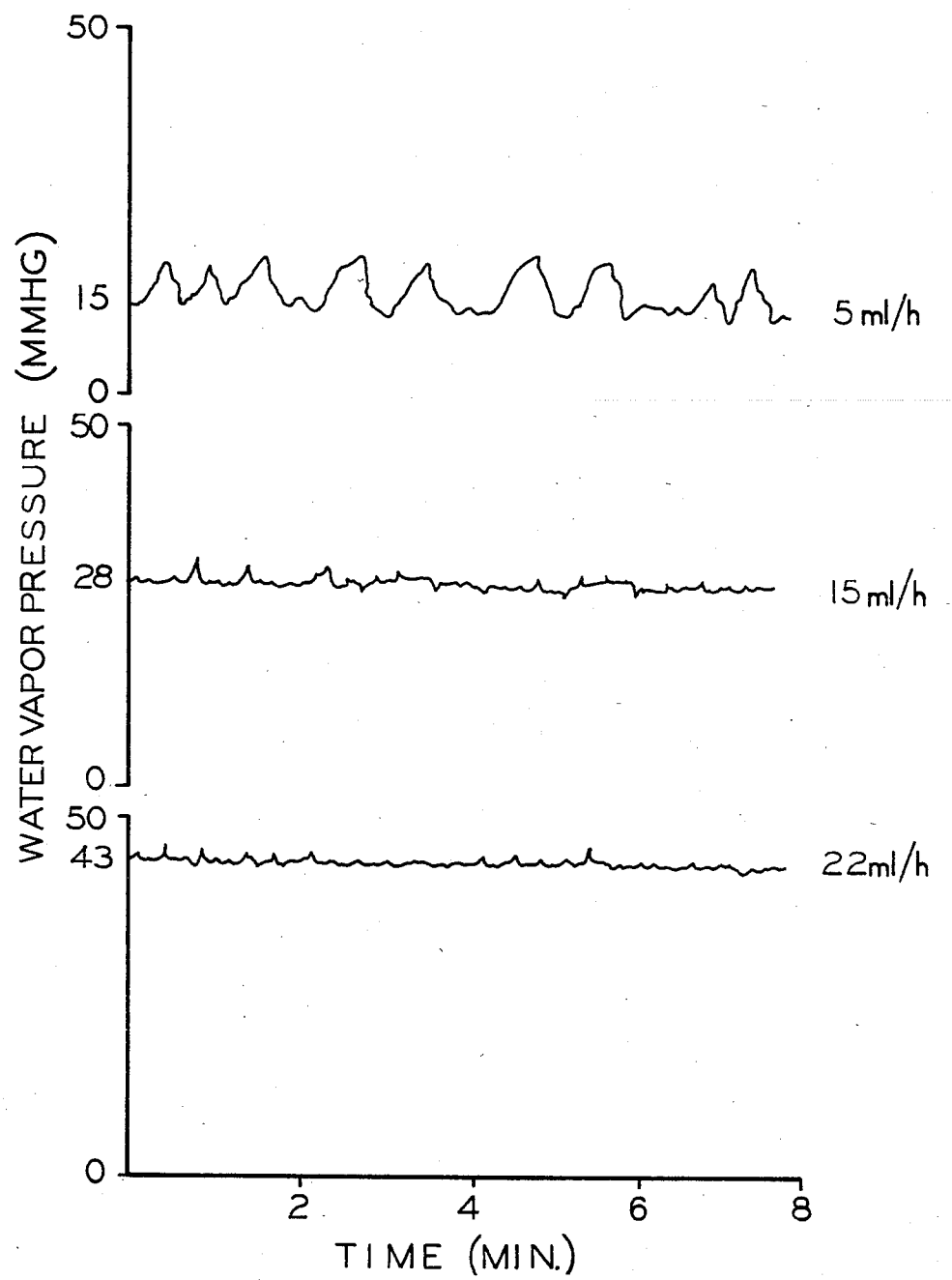
FIG. 6 is a graph, showing the test results of variations in injected water flow rates on the water vapor pressure of the jet gas.

The effect of variations in injected water flowrates is shown in FIG. 6. At low flowrates, large vacillations in the water vapor output occurred, corresponding to intermittent drops of water passing through the heat exchanger (5 drops/min at 5 ml/h). As the water flowrate was increased to 22 ml/h, the RH increased and became more stable, attaining a maximum value of 91% at 37° C.

To check these results, the amount of injected water per liter of jet gas was compared to the calculated absolute humidity of gas in the sample chamber. At a water injection rate of 22 ml/h and a jet flow of 8 l/min, each liter of gas contained approximately 46 mg of water. This compared favorably with the expected absolute humidity of 40 mg/l for gas that is 91% saturated at 37° C. The difference of 6 mg/l was probably accounted for in part by water particles carried by the gas that were too small to be visible and by slight errors in measurement of temperature and water vapor pressure.

In application of the system of the present invention, the temperature of the jet gas (measured as previously described) is maintained at 35°–37° C. The temperature of the jet gas is affected by several factors, including the temperature of the heat exchanger, the total flow of the jet gas, the temperature and injection rate of the water, and the temperature and flowrate of the continuous positive airway pressure gas. These factors may be adjusted so that the desired amount of water is injected into the jet gas without visible condensation on the walls of the delivery tube. The following sequence of steps is effective during the initial setup of the system before its connection to the patient: first, set the continuous positive airway pressure circuit gas flow and temperature to the desired levels; then, determine the jet ventilation variables (ie, frequency, driving pressure, and duty cycle), according to the patient's condition; once the total jet flow is set, adjust the temperature of the jet gas by varying the temperature of the heat exchanger and increase the water injection rate to the desired amount; and, make any final adjustments after the patient is connected to the ventilator.

The above-detailed description of the present invention is made for explanatory purposes. It is understood that various modifications to the apparatus may be made without departing from the object and scope of the following claims.

What we claim is:

1. An improved method for delivering a mixture of respirable air to a patient comprising the following steps:
   blending a supply of gases containing at least air and oxygen;
   heating and humidifying a first stream of said air-oxygen mixture;
   pressurizing a second stream of said air-oxygen mixture;
   heating said second stream of said air-oxygen mixture;
   pulsating said heated second stream of said air-oxygen mixture;
   injecting water into said heated, pulsating second stream of said air-oxygen mixture;
   heating said heated, pulsating second stream of said air-oxygen mixture containing said water such that said water in said heated, pulsating second stream of said air-oxygen mixture is vaporized; and
   delivering said heated first stream of said air-oxygen mixture and said heated pulsating second stream of said air-oxygen mixture containing said vaporized water to a patient.

2. An improved ventilator humidification system for use with a high frequency jet ventilation humidification system for delivering a mixture of heated and humidified respirable air to a patient, said ventilation humidification system comprising, in combination:
   a supply means providing a first stream and a second stream of said respirable air mixture;
   a humidifier means in communication with said supply means for receiving said first stream of said air mixture from said supply means, said humidification means heating and humidifying said first stream of said air mixture;

a heating means in communication with said supply means for receiving said second sstream of said air mixture from said supply means, said heating means heating said second stream of said air mixture;

a control means in communication with said heating means for receiving said heated second stream of said air mixture from said heating means, said control means regulating the flow of said second stream of said air mixture such that said control means pressurizes and pulsates said heated second stream of said air mixture;

a water injection means in communication with said control means for receiving said heated, pulsating second stream of said air mixture from said control means, said water injection means injecting water into said heated, pulsating second stream of said air mixture, said water injection means thereafter returning said heated, pulsating second stream of said air mixture containing said injected water to said heating means whereby said heating means vaporizes said injected water in said heated, pulsating second stream into said air mixture; and, a delivery means in communication with said humidifier means for receiving said heated and humidified first stream of said air mixture from said humidifier means, said delivery means in communication with said heating means for receiving said heated, pulsating second stream of said air mixture containing said vaporized water from said heating means, said delivery means receiving said first and said second streams such that said first stream heats said second sstream within said delivery means, said delivery means thereafter simultaneously delivering said first stream and second stream to a patient.

3. The improved ventilator humidification system of claim 2 further including a regulating means in communication with said supply means for receiving said second stream of said air mixture from said supply means, said regulator means regulating the flow of said second stream of said air mixture such that said regulating means pressurizes said second stream of said air mixture; said regulating means in commumication with said heating means such that said heating means thereafter receives said pressurized, second stream of said air mixture from said regulating means and heats said pressurized second stream of said air mixture.

* * * * *